United States Patent [19]

McKittrick et al.

[11] Patent Number: 5,624,920

[45] Date of Patent: Apr. 29, 1997

[54] SULFUR-SUBSTITUTED AZETIDINONE COMPOUNDS USEFUL AS HYPOCHOLESTEROLEMIC AGENTS

[75] Inventors: Brian A. McKittrick, Bloomfield; Sundeep Dugar, Bridgewater; Duane A. Burnett, Fanwood, all of N.J.

[73] Assignee: Schering Corporation, Kenilworth, N.J.

[21] Appl. No.: 342,197

[22] Filed: Nov. 18, 1994

[51] Int. Cl.$^6$ ..................... C07D 205/08; A61K 31/395
[52] U.S. Cl. ........................................... 514/210; 540/360
[58] Field of Search ........................... 514/210; 540/360

[56] References Cited

U.S. PATENT DOCUMENTS

| | | | |
|---|---|---|---|
| 4,680,391 | 7/1987 | Firestone et al. | 540/355 |
| 4,983,597 | 1/1991 | Yang et al. | 514/210 |
| 5,120,729 | 6/1992 | Chabala et al. | 514/210 |

FOREIGN PATENT DOCUMENTS

| | | |
|---|---|---|
| 199630 | 10/1986 | European Pat. Off. |
| 264231 | 4/1988 | European Pat. Off. |
| 337549 | 10/1989 | European Pat. Off. |
| 93/02048 | 2/1993 | WIPO |
| 94/14433 | 7/1994 | WIPO |
| WO95/08532 | 3/1995 | WIPO |
| WO95/26334 | 10/1995 | WIPO |

OTHER PUBLICATIONS

Bose et al, *Org. Magn. Reson.*, 12, 1 (1979), pp. 34–38.
Harwood et al, *Journal of Lipid Research*, 34 (1993), pp. 377–395.
Atherosclerosis, 115 (1995), pp. 45–63.
*Biochemical Pharmacology*, 47, 9 (1994), pp. 1545–1551.
Allain, et al, *Clin. Chem.*, 20, (1974), pp. 470–475.
Schnitzer–Polokoff, et al, *Comp. Biochem. Physiol.*,99A (1991), pp. 665–670.
Horie, et al, *Atherosclerosis*, 88 (1991), pp. 183–192.
Baxter, et al, *J. Biological Chem.*, 267, 17 (1992), pp. 11705–11708.
*Current Drugs: Anti–Atheroschlerotic Agents*–Summary Factfile, May, 1992. pp. A–5 to A–23.
Ram et al, *Indian J. Chem.*, Sect B, 29b, 12 (1990), pp. 1134–1137.
Witzum, *Circulation*, 80, 5 (1989), pp. 1101–1114.
Illingworth, *Drugs* 36(Supp. 3) (1988), pp. 63–71.
Bose, *Tetrahedron Letters* 1972, 3594–3602.

Primary Examiner—Mark L. Berch
Attorney, Agent, or Firm—Anita M. Magatti; Eric S. Dicker

[57] ABSTRACT

Sulfur-substituted azetidinone hypocholesterolemic agents of the formula

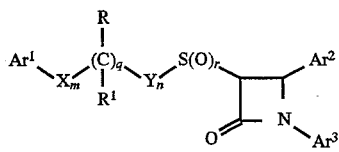

or a pharmaceutically acceptable salt thereof, wherein:

$Ar^1$ is aryl or $R^{10}$-substituted aryl;
$Ar^2$ is aryl or $R^4$-substituted aryl;
$Ar^3$ is aryl or $R^5$-substituted aryl;
X and Y are —$CH_2$—, —CH(lower alkyl)— or —C(dilower alkyl)—;
R is —$OR^6$, —O(CO)$R^6$, —O(CO)O$R^9$ or —O(CO)N$R^6R^7$; $R^1$ is hydrogen, lower alkyl or aryl; or R and $R^1$ together are =O;
q is 0 or 1; r is 0, 1 or 2; m and n are 0–5; provided that the sum of m, n and q is 1–5;
$R^4$ is selected from lower alkyl, —$OR^6$, —O(CO)$R^6$, —O(CO)O$R^9$, —O($CH_2$)$_{1-5}$O$R^6$, —O(CO)N$R^6R^7$, —N$R^6R^7$, —$NR^6$(CO)$R^7$, —$NR^6$(CO)O$R^9$, —$NR^6$(CO)N$R^7R^8$, —$NR^6SO_2R^9$, —COO$R^6$, —CON$R^6R^7$, —CO$R^6$, —$SO_2NR^6R^7$, S(O)$_{0-2}R^9$, —O($CH_2$)$_{1-10}$—COO$R^6$, —O($CH_2$)$_{1-10}$CON$R^6R^7$, —(lower alkylene)COO$R^6$ and —CH=CH—COO$R^6$;
$R^5$ is selected from —$OR^6$, —O(CO)$R^6$, —O(CO)O$R^9$, —O($CH_2$)$_{1-5}$O$R^6$, —O(CO)N$R^6R^7$, —N$R^6R^7$, —$NR^6$(CO)$R^7$, —$NR^6$(CO)O$R^9$, —$NR^6$(CO)N$R^7R^8$, —$NR^6SO_2R^9$, —COO$R^6$, —CON$R^6R^7$, —CO$R^6$, —$SO_2NR^6R^7$, S(O)$_{0-2}R^9$, —O($CH_2$)$_{1-10}$—COO$R^6$, —O($CH_2$)$_{1-10}$CON$R^6R^7$, —$CF_3$, —CN, —$NO_2$, halogen, —(lower alkylene)COO$R^6$ and —CH=CH—COO$R^6$;
$R^6$, $R^7$ and $R^8$ are H, lower alkyl, aryl or aryl-substituted lower alkyl;
$R^9$ is lower alkyl, aryl or aryl-substituted lower alkyl; and
$R^{10}$ is selected from lower alkyl, —$OR^6$, —O(CO)$R^6$, —O(CO)O$R^9$, —O($CH_2$)$_{1-5}$O$R^6$, —O(CO)N$R^6R^7$, —N$R^6R^7$, —$NR^6$(CO)$R^7$, —$NR^6$(CO)O$R^9$, —$NR^6$(CO)N$R^7R^8$, —$NR^6SO_2R^9$, —COO$R^6$, —CON$R^6R^7$, —CO$R^6$, —$SO_2NR^6R^7$, S(O)$_{0-2}R^9$, —O($CH_2$)$_{1-10}$—COO$R^6$, —O($CH_2$)$_{1-10}$CON$R^6R^7$, —$CF_3$, —CN, —$NO_2$ and halogen;

are disclosed, as well as pharmaceutical compositions containing them, and a method of lowering serum cholesterol by administering said compounds, alone or in combination with a cholesterol biosynthesis inhibitor.

15 Claims, No Drawings

SULFUR-SUBSTITUTED AZETIDINONE COMPOUNDS USEFUL AS HYPOCHOLESTEROLEMIC AGENTS

BACKGROUND OF THE INVENTION

The present invention relates to sulfur-substituted azetidinones useful as hypocholesterolemic agents in the treatment and prevention of atherosclerosis, and to the combination of a sulfur-substituted azetidinone of this invention and a cholesterol biosynthesis inhibitor for the treatment and prevention of atherosclerosis.

Atherosclerotic coronary heart disease (CHD) represents the major cause for death and cardiovascular morbidity in the western world. Risk factors for atherosclerotic coronary heart disease include hypertension, diabetes mellitus, family history, male gender, cigarette smoke and serum cholesterol. A total cholesterol level in excess of 225–250 mg/dl is associated with significant elevation of risk of CHD.

Cholesteryl esters are a major component of atherosclerotic lesions and the major storage form of cholesterol in arterial wall cells. Formation of cholesteryl esters is also a key step in the intestinal absorption of dietary cholesterol. Thus, inhibition of cholesteryl ester formation and reduction of serum cholesterol is likely to inhibit the progression of atherosclerotic lesion formation, decrease the accumulation of cholesteryl esters in the arterial wall, and block the intestinal absorption of dietary cholesterol.

A few azetidinones have been reported as being useful in lowering cholesterol and/or in inhibiting the formation of cholesterol-containing lesions in mammalian arterial walls. U.S. Pat. No. 4,983,597 discloses N-sulfonyl-2-azetidinones as anticholesterolemic agents and Ram, et al., in *Indian J. Chem. Sect. B.* 29B, 12 (1990), p. 1134–7, disclose ethyl 4-(2-oxoazetidin-4-yl)phenoxy-alkanoates as hypolipidemic agents. European Patent Publication 264,231 discloses 1-substituted-4-phenyl-3-(2-oxo-alkylidene)-2-azetidinones as blood platelet aggregation inhibitors.

European Patent 199,630 and European Patent Application 337,549 disclose elastase inhibitory substituted azetidinones said to be useful in treating inflammatory conditions resulting in tissue destruction which are associated with various disease states, e.g. atherosclerosis.

WO93/02048, published Feb. 4, 1993, discloses substituted β-lactams useful as hypocholesterolemic agents. WO94/14433, published Jul. 7, 1994, discloses the combination of substituted β-lactams as defined in WO93/02048 with cholesterol biosynthesis inhibitors.

The regulation of whole-body cholesterol homeostasis in humans and animals involves the regulation of dietary cholesterol and modulation of cholesterol biosynthesis, bile acid biosynthesis and the catabolism of the cholesterol-containing plasma lipoproteins. The liver is the major organ responsible for cholesterol biosynthesis and catabolism and for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis.

When intestinal cholesterol absorption is reduced, by whatever means, less cholesterol is delivered to the liver. The consequence of this action is decreased hepatic lipoprotein (VLDL) production and an increase in the hepatic clearance of plasma cholesterol, mostly as LDL. Thus, the net effect of inhibiting intestinal cholesterol absorption is a decrease in plasma cholesterol levels.

The inhibition of cholesterol biosynthesis by 3-hydroxy-3-methylglutaryl coenzyme A (HMG CoA) reductase (EC1.1.1.34) inhibitors has been shown to be an effective way to reduce plasma cholesterol (Witzum, *Circulation*, 80, 5 (1989), p. 1101–1114) and reduce atherosclerosis. Combination therapy of an HMG CoA reductase inhibitor and a bile acid sequestrant has been demonstrated to be more effective in human hyperlipidemic patients than either agent in monotherapy (Illingworth, *Drugs*, 36 (Suppl. 3) (1988), p. 63–71).

SUMMARY OF THE INVENTION

Hypocholesterolemic compounds of the present invention are represented by the formula I

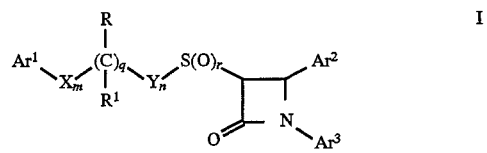

or a pharmaceutically acceptable salt thereof, wherein:

$Ar^1$ is aryl or $R^{10}$-substituted aryl;

$Ar^2$ is aryl or $R^4$-substituted aryl;

$Ar^3$ is aryl or $R^5$-substituted aryl;

X and Y are independently selected from the group consisting of —CH$_2$—, —CH(lower alkyl)— and —C(dilower alkyl)—;

R is —OR$^6$, —O(CO)R$^6$, —O(CO)OR$^9$ or —O(CO)NR$^6$R$^7$; R$^1$ is hydrogen, lower alkyl or aryl; or R and R$^1$ together are =O;

q is 0 or 1;

r is 0, 1 or 2;

m and n are independently 0, 1, 2, 3, 4 or 5; provided that the sum of m, n and q is 1, 2, 3, 4 or 5;

$R^4$ is 1–5 substituents independently selected from the group consisting of lower alkyl, —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, —S(O)$_{0-2}$R$^9$, —O(CH$_2$)$_{1-10}$—COOR$^6$, —O(CH$_2$)$_{1-10}$CONR$^6$R$^7$, —(lower alkylene)COOR$^6$ and —CH=CH—COOR$^6$;

$R^5$ is 1–5 substituents independently selected from the group consisting of —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$R$^9$, —O(CH$_2$)$_{1-10}$—COOR$^6$, —O(CH$_2$)$_{1-10}$CONR$^6$R$^7$, —CF$_3$, —CN, —NO$_2$, halogen, —(lower alkylene)COOR$^6$ and —CH=CH—COOR$^6$;

$R^6$, $R^7$ and $R^8$ are independently selected from the group consisting of hydrogen, lower alkyl, aryl and aryl-substituted lower alkyl;

$R^9$ is lower alkyl, aryl or aryl-substituted lower alkyl; and $R^{10}$ is 1–5 substituents independently selected from the group consisting of lower alkyl, —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$R$^9$, —O(CH$_2$)$_{1-10}$—

$COOR^6$, $-O(CH_2)_{1-10}CONR^6R^7$, $-CF_3$, $-CN$, $-NO_2$ and halogen.

Within the scope of formula I, there are two preferred structures. In formula IA, q is zero and the remaining variables are as defined above, and in formula IB, q is 1 and the remaining variables are as defined above:

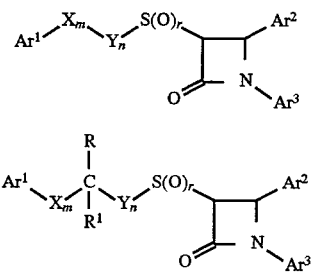

$R^4$, $R^5$ and $R^{10}$ are each preferably 1–3 independently selected substituents. Preferred are compounds of formula I wherein $Ar^1$ is phenyl or $R^{10}$-substituted phenyl, especially (4-$R^{10}$)-substituted phenyl. $Ar^2$ is preferably $R^4$-substituted phenyl, especially (4-$R^4$)-substituted phenyl. $Ar^3$ is preferably phenyl or $R^5$-substituted phenyl, especially (4-$R^5$)-substituted phenyl. When $Ar^1$ is $R^{10}$-substituted phenyl, $R^{10}$ is preferably halogeno, especially fluoro. When $Ar^2$ is $R^4$-substituted phenyl, $R^4$ is preferably $-OR^6$, especially wherein $R^6$ is hydrogen or lower alkyl. When $Ar^3$ is $R^5$-substituted phenyl, $R^5$ is preferably halogeno, especially fluoro. Especially preferred are compounds of formula I wherein $Ar^1$ is phenyl or 4-fluorophenyl, $Ar^2$ is 4-(alkoxy or hydroxy)phenyl, and $Ar^3$ is phenyl or 4-fluorophenyl.

X and Y are each preferably $-CH_2-$. The sum of m, n and q is preferably 2, 3 or 4, more preferably 2. When q is 1, n is preferably 1 to 5.

Preferences for X, Y, $Ar^1$, $Ar^2$ and $Ar^3$ are the same in each of formulae IA and IB.

In compounds of formula IA, the sum of m and n is preferably 2, 3 or 4, more preferably 2. Also preferred are compounds wherein the sum of m and n is 2, and r is 0 or 1.

In compounds of formula IB, the sum of m and n is preferably 1, 2 or 3, more preferably 1. Especially preferred are compounds wherein m is zero and n is 1. $R^1$ is preferably hydrogen and R is preferably $-OR^6$ wherein $R^6$ is hydrogen, or a group readily metabolizable to a hydroxyl (such as $-O(CO)R^6$, $-O(CO)OR^9$ and $-O(CO)NR^6R^7$, defined above), or R and $R^1$ together form a =O group.

This invention also relates to a method of lowering the serum cholesterol level in a mammal in need of such treatment comprising administering an effective amount of a compound of formula I. That is, the use of a compound of the present invention as an hypocholesterolemic agent is also claimed.

In still another aspect, the present invention relates to a pharmaceutical composition comprising a serum cholesterol-lowering effective amount of a compound of formula I in a pharmaceutically acceptable carrier.

The present invention also relates to a method of reducing plasma cholesterol levels, and to a method of treating or preventing atherosclerosis, comprising administering to a mammal in need of such treatment an effective amount of a combination of a sulfur-substituted azetidinone cholesterol absorption inhibitor of formula I and a cholesterol biosynthesis inhibitor. That is, the present invention relates to the use of a sulfur-substituted azetidinone cholesterol absorption inhibitor of formula I for combined use with a cholesterol biosynthesis inhibitor (and, similarly, use of a cholesterol biosynthesis inhibitor for combined use with a sulfur-substituted azetidinone cholesterol absorption inhibitor of formula I) to treat or prevent atherosclerosis or to reduce plasma cholesterol levels.

In yet another aspect, the invention relates to a pharmaceutical composition comprising an effective amount of a sulfur-substituted azetidinone cholesterol absorption inhibitor of formula I, a cholesterol biosynthesis inhibitor, and a pharmaceutically acceptable carrier. In a final aspect, the invention relates to a kit comprising in one container an effective amount of a sulfur-substituted azetidinone cholesterol absorption inhibitor of formula I in a pharmaceutically acceptable carrier, and in a separate container, an effective amount of a cholesterol biosynthesis inhibitor in a pharmaceutically acceptable carrier.

DETAILED DESCRIPTION

As used herein, the term "lower alkyl" means straight or branched alkyl chains of 1 to 6 carbon atoms.

"Aryl" means phenyl, naphthyl, indenyl, tetrahydronaphthyl or indanyl.

"Halogeno" means fluorine, chlorine, bromine or iodine atoms.

The above statement, wherein $R^6$, $R^7$ and $R^8$ are said to be independently selected from a group of substituents, means that $R^6$, $R^7$ and $R^8$ are independently selected, but also that where an $R^6$, $R^7$ or $R^8$ variable occurs more than once in a molecule, those occurrences are independently selected (e.g., if R is $-OR^6$ wherein $R^6$ is hydrogen, $R^4$ can be $-OR^6$ wherein $R^6$ is lower alkyl).

Compounds of the invention have at least one asymmetric atom and therefore all isomers, including enantiomers and diastereomers are contemplated as being part of this invention. The invention includes d and I isomers in both pure form and in admixture, including racemic mixtures. Isomers can be prepared using conventional techniques, either by reacting chiral starting materials or by separating isomers of a compound of formula I. Isomers may also include geometric isomers, e.g. when a double bond is present. All such geometric isomers are contemplated for this invention.

Those skilled in the art will appreciate that for some compounds of formula I, one isomer will show greater pharmacological activity than another isomer.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base form for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Cholesterol biosynthesis inhibitors for use in the combination of the present invention include HMG CoA reductase inhibitors such as lovastatin, pravastatin, fluvastatin, simvastatin, and CI-981; HMG CoA synthetase inhibitors, for example L-659,699 ((E,E)-11-[3'R-(hydroxy-methyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl)methoxy]benzene-methanamine hydrochloride) and other cholesterol biosynthesis inhibitors such as DMP-565. Preferred HMG CoA reductase inhibitors are lovastatin, pravastatin and simvastatin.

Compounds of formula I can be prepared by known methods, for example those described below.

Method A

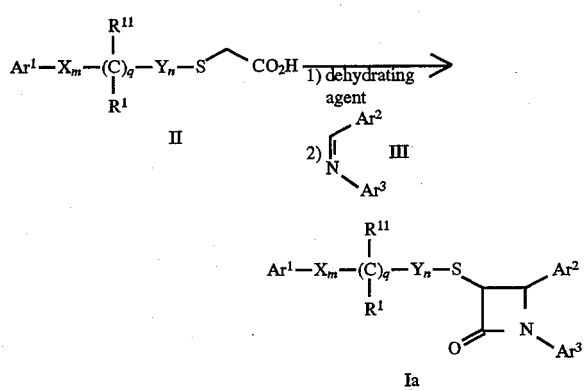

Compounds of formula I wherein r is zero, $R^{11}$ is a protected hydroxy group, wherein the protecting groups are as defined below in Table 1, and the remaining variables are as defined above, i.e., compounds of formula Ia, can be prepared according to the above reaction scheme, wherein a carboxylic acid of formula II is reacted with an imine of formula III in the presence of a base such as triethylamine and a suitable dehydrating agent such as dimethylphosphoramidous dichloride. The resultant compound is treated with an acid such as hydrofluoric acid to obtain the thio compound of formula Ia. When the protected hydroxy group $R^{11}$ is an alkoxy or benzyloxy group, such a protecting group need not be removed to obtain a compound of formula I, but other protecting groups can be removed using conventional techniques to obtain compounds of formula I wherein R is hydroxy.

Compounds wherein R is hydroxy can be converted by well known techniques to other compounds of formula I wherein R is functionalized, i.e., it is —$OR^{6a}$, —$O(CO)R^6$, —$O(CO)OR^9$, or —$O(CO)NR^6R^7$, wherein $R^6$, $R^7$ and $R^9$ are as defined above and $R^{6a}$ is lower alkyl, aryl, or aryl-lower alkyl. For example, treatment of the alcohol with an alkyl halide in the presence of a suitable base such as NaH will afford alkoxy-substituted compounds (i.e., R or $R^2$ is $OR^6$, wherein $R^6$ is lower alkyl); treatment of the alcohol with an acylating agent such as acetylchloride will result in compounds wherein R or $R^2$ is —$OC(O)R^6$; treatment of the alcohol with phosgene followed by an alcohol of the formula $HOR^9$ affords compounds substituted with a —$OC(O)OR^9$ group; and treatment of the alcohol with phosgene followed by an amine of the formula $HNR^6R^7$ affords compounds wherein R or $R^2$ is —$OC(O)N R^6R^7$.

Compounds of formula Ia wherein q is 1, and R and $R^1$ form an =O group can be converted to the corresponding compounds wherein $R^1$ is hydrogen and R is OH by treatment with a reducing agent such as sodium borohydride.

To prepare the corresponding sulfinyl compounds, i.e., compounds of formula I wherein r is 1, and the remaining variables are as defined above (compounds of formula Ib), treat the hydroxy-protected thio compound of formula Ia with 1 equivalent of an oxidant such as a peracid, e.g., m-chloroperbenzoic acid, or sodium metaperiodate:

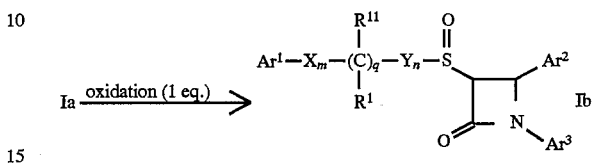

To prepare the corresponding sulfonyl compounds, i.e., compounds of formula I wherein r is 2, and the remaining variables are as defined above (compounds of formula Ic), treat the hydroxy-protected thio compound of formula Ia with 2 equivalents of an oxidant as described above:

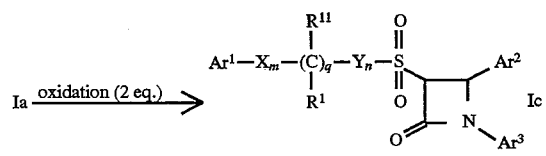

Compounds of fomulae Ib and Ic can be deprotected at $R^{11}$ as necessary to obtain compounds of formula I.

Method B

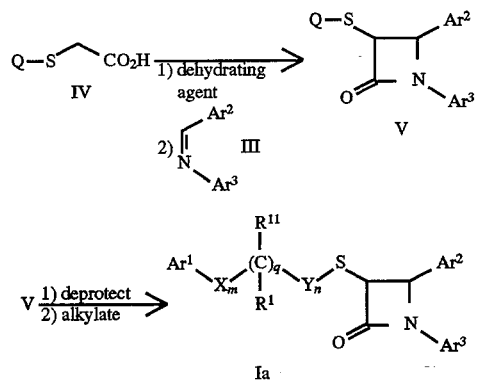

Compounds of formula Ia, wherein the variables are as defined above, can be prepared by reacting a protected mercaptoacetic acid of formula IV, wherein Q is a sulfur-protecting group such as benzyl or substituted-benzyl, with an imine as described in Method A. The protecting group Q is then removed, and the mercapto group is alkylated with a compound of the formula

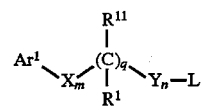

wherein L is a leaving group such as bromo or iodo.

Using the methods described in Method A, compounds of formula Ia prepared by Method B can be converted to sulfinyl and sulfonyl compounds, compounds wherein R and $R^1$ are =O can be converted to compounds wherein R is H and $R^1$ is OH, and compounds wherein R is hydroxy can be converted to functionalized hydroxy groups.

Method C

Compounds of formula I wherein r is zero and the remaining variables are as defined above can be prepared in an enantioselective manner as follows:

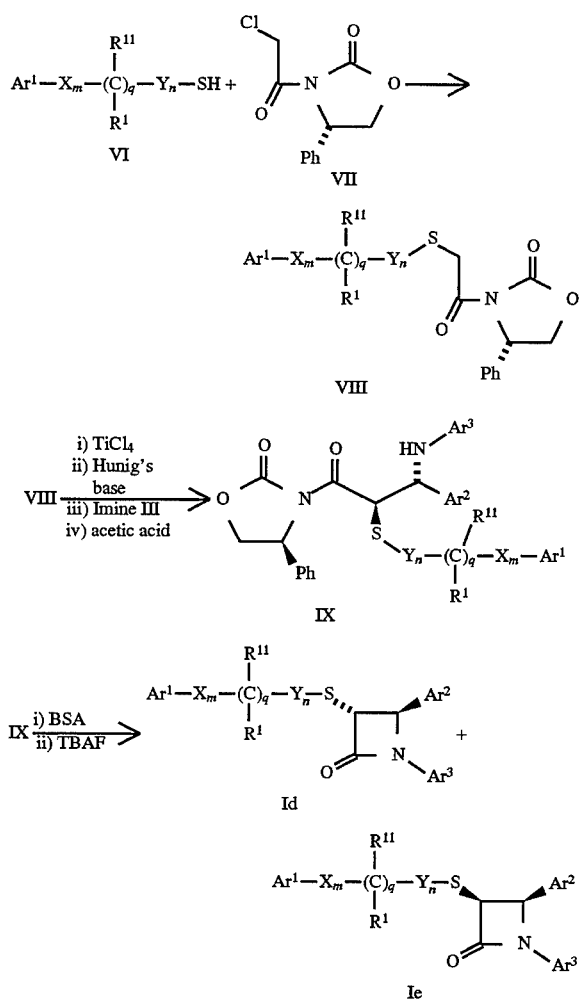

The chloroacylated oxizolidinone auxiliary of formula VII is reacted with the mercaptan of formula VI, wherein the variables are as defined above, in the presence of a base such as triethylamine in an inert solvent such as $CH_2Cl_2$. The resultant compound of formula VIII is treated with $TiCl_4$ in the presence of a base such as diisopropylethylamine (Hunig's base), reacted with an imine of formula III, and then the reaction is quenched with an acid such as acetic acid. The resulting compound of formula IX is then cyclized by reaction with a silylating agent such as bis(trimethylsilyl) acetamide (BSA) and a fluoride catalyst such as tetra butyl ammonium fluoride (TBAF). The cyclization product is separated into cis and trans isomers of formulae Id and Ie using conventional purification techniques, e.g., flash chromatography.

Compounds of formulae Id and Ie can be converted to the corresponding sulfinyl and sulfonyl compounds by reaction with a peracid as described above or with a reagent such as (R) or (S) (10-camphor-sulfonyl)-oxaziridine. For example, a compound of formula Id can be converted to the corresponding sulfinyl compounds, If and Ig, as follows:

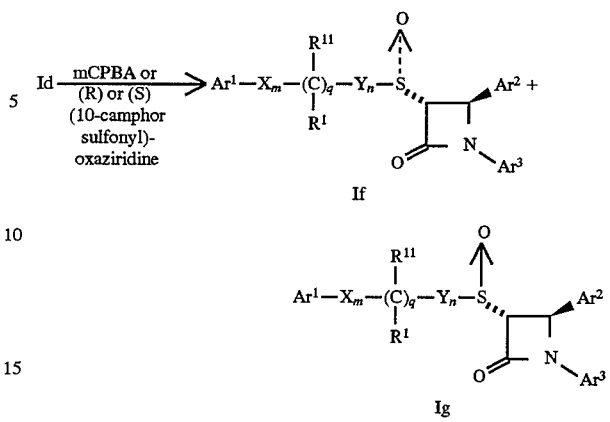

Before or after separation into cis and trans isomers, as suitable, compounds of formulae Id and Ie can be deprotected at $R^{11}$, and compounds wherein R is OH can be functionalized as described in Method A.

Starting compounds II, III, IV, VI and VII are all either commercially available, well known in the art, or are prepared via known methods.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| \>NH | \>NCOalkyl, \>NCObenzyl, \>NCOphenyl |
|  | \>NCH$_2$OCH$_2$CH$_2$Si(CH$_3$)$_3$, \>NC(O)OC(CH$_3$)$_3$, |
|  | \>N-benzyl, \>NSi(CH$_3$)$_3$, \>NSi—C(CH$_3$)$_3$ with CH$_3$ groups |
| —NH$_2$ | —N(succinimide) |
| —OH | —OCH$_3$, —OCH$_2$OCH$_3$, —OSi—C(CH$_3$)$_3$ with CH$_3$ groups |
|  | —OSi(CH$_3$)$_3$, or —OCH$_2$phenyl |

We have found that the compounds of this invention lower serum lipid levels, in particular serum cholesterol levels. Compounds of this invention have been found to inhibit the intestinal absorption of cholesterol and to significantly reduce the formation of liver cholesteryl esters in animal models. Thus, compounds of this invention are hypocholesterolemic agents by virtue of their ability to inhibit the intestinal absorption and/or esterification of cholesterol; they are, therefore, useful in the treatment and prevention of atherosclerosis in mammals, in particular in humans.

The in vivo activity of the compounds of formula I can be determined by the following procedure:

In Vivo Assay of Hypolipidemic Agents Using the Hyperlipidemic Hamster

Hamsters are separated into groups of six and given a controlled cholesterol diet (Purina Chow #5001 containing 0.5% cholesterol) for seven days. Diet consumption is monitored to determine dietary cholesterol exposure in the face of test compounds. The animals are dosed with the test compound once daily beginning with the initiation of diet. Dosing is by oral gavage of 0.2 mL of corn oil alone (control group) or solution (or suspension) of test compound in corn oil. All animals moribund or in poor physical condition are euthanized. After seven days, the animals are anesthetized by intramuscular (IM) injection of ketamine and sacrificed by decapitation. Blood is collected into vacutainer tubes containing EDTA for plasma lipid analysis and the liver excised for tissue lipid analysis. Lipid analysis is conducted as per published procedures (Schnitzer-Polokoff, R., et al, Comp. Biochem. Physiol., 99A, 4 (1991), p. 665–670) and data is reported as percent reduction of lipid versus control.

The present invention also relates to a pharmaceutical composition comprising a compound of formula I and a pharmaceutically acceptable carrier. The compounds of formula I can be administered in any conventional dosage form, preferably an oral dosage form such as a capsule, tablet, powder, cachet, suspension or solution. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily hypocholesteremic dose of a compound of formula I is about 0.1 to about 30 mg/kg of body weight per day, preferably about 0.1 to about 15 mg/kg. For an average body weight of 70 kg, the dosage level is therefore from about 5 mg to about 1000 mg of drug per day, given in a single dose or 2-4 divided doses. The exact dose, however, is determined by the attending clinician and is dependent on the potency of the compound administered, the age, weight, condition and response of the patient.

For the combinations of this invention wherein the sulfur-substituted azetidinone is administered in combination with a cholesterol biosynthesis inhibitor, the typical daily dose of the cholesterol biosynthesis inhibitor is 0.1 to 80 mg/kg of mammalian weight per day administered in single or divided dosages, usually once or twice a day: for example, for HMG-CoA reductase inhibitors, about 10 to about 40 mg per dose is given 1 to 2 times a day, giving a total daily dose of about 10 to 80 mg per day, and for the other cholesterol biosynthesis inhibitors, about 1 to 1000 mg per dose is given 1 to 2 times a day, giving a total daily dose of about 1 mg to about 2000 mg per day. The exact dose of any component of the combination to be administered is determined by the attending clinician and is dependent on the potency of the compound administered, the age, weight, condition and response of the patient.

Where the components of a combination are administered separately, the number of doses of each component given per day may not necessarily be the same, e.g. where one component may have a greater duration of activity, and will therefore need to be administered less frequently.

Since the present invention relates to the reduction of plasma cholesterol levels by treatment with a combination of active ingredients wherein said active ingredients may be administered separately, the invention also relates to combining separate pharmaceutical compositions in kit form. That is, a kit is contemplated wherein two separate units are combined: a cholesterol biosynthesis inhibitor pharmaceutical composition and a sulfur-substituted azetidinone cholesterol absorption inhibitor pharmaceutical composition. The kit will preferably include directions for the administration of the separate components. The kit form is particularly advantageous when the separate components must be administered in different dosage forms (e.g. oral and parenteral) or are administered at different dosage intervals.

Following are examples of preparing compounds of formula I. The terms cis and trans refer to the relative orientations at the azetidinone 3- and 4-positions unless otherwise indicated. The term "J" refers to the proton NMR coupling constant in hertz (Hz) between the 3- and 4-substituted protons of the azetidinone. CD spectra were obtained as solutions in methanol.

EXAMPLE 1

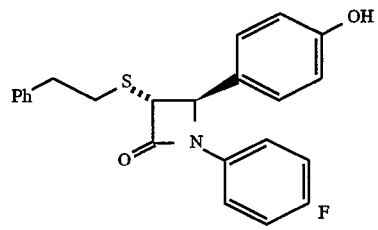

Step 1:

Heat a mixture of 4-fluoroaniline (128 ml) and 4-t-butyldimethylsiloxy benzaldehyde (290 g) in toluene (1.2 L) to reflux under a Dean-Stark trap. After 24 h, concentrate in vacuo and dissolve the residue in warm hexane (0.2 L). Cool to −20° C. and collect the resultant imine (378 g, 94% yield) by filtration; mp 51.4°–52.2° C.

Step 2:

To a mixture of phenethylmercapto acetic acid (0.55 g) [prepared in two steps by i) reaction of phenethyl mercaptan and ethyl bromoacetate and ii) saponification with ethanolic aqueous NaOH], the imine prepared in step 1 and triethylamine (TEA) (1.2 ml) in $CH_2Cl_2$ (20 ml), add dimethylaminophosphoryldichloride at 0° C. Stir overnight while allowing the reaction to warm to room temperature (rt). Partition the mixture between ethyl acetate (EtOAc) and 10% $NaHCO_3$. Wash ($H_2O$), dry ($MgSO_4$) and concentrate the organic layer, then purify the residue by flash chromatography on silica using hexane/EtOAc (20:1) to obtain a yellow oil (0.48 g, 34%). Resolve this oil by HPLC with a Chiralcel OD column using hexane/isopropyl alcohol (66:1) and collect the second peak.

Step 3:

Treat the product of step 2 (215 mg) in $CH_3CN$ (21 ml) at 0° C. with 48% HF (2.5 ml). Stir overnight while allowing the reaction to warm to rt. Partition the mixture between ether ($Et_2O$) and cold water and wash the organic layers with 10% $NaHCO_3$ and water. Dry ($MgSO_4$) and concentrate the organic layer and purify the residue by flash chromatography on silica using hexane/EtOAc (5:1) to collect the title compound (1) as a colorless solid (0.16 g, 96%). SIMS 394 (M+H), 256 (100%); Elemental analysis calculated for $C_{23}H_{20}NO_2SF \cdot 0.25H_2O$: C 69.41, H 5.19, N 3.52; found C 69.42, H 5.26, N 3.45; $[\alpha]_D^{25}$=+44.8° (1.25 mg/ml $CH_3OH$); 1H NMR $CDCL_3$: 2.95 (m, 4H), 3.93 (d, J=2.4 Hz, 1H), 4.67 (d, J=2.4 Hz, 1H), 5.06 (s, 1H), 6.85 (d, 1H), 6.92 (dd, 2H), 7.15–7.3 (9H).

Method B

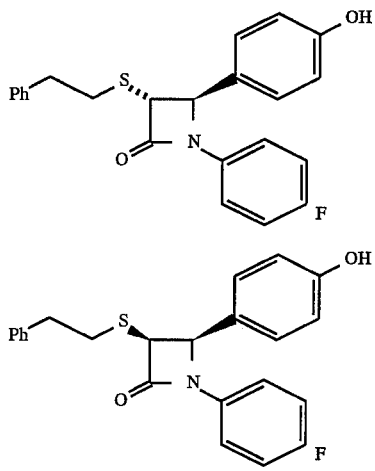

Step 1:

Add dropwise a solution of chloroacetyl chloride (9.76 ml) in CH$_2$Cl$_2$ (110 ml) to a 0° C. solution of (S)-4-phenyl oxazolidinone (10.0 g), TEA (35 ml) and dimethylaminopyridine (DMAP) (0.5 g) in CH$_2$Cl$_2$ (150 ml). Gradually warm the reaction to rt, then add silica gel (approx. 50 g) and concentrate in vacuo. Purify the residue by flash chromatography on silica using EtOAc/hexane (1:4) to give a colorless solid (11.3 g, 77%).

Step 2:

Add phenethyl mercaptan to a solution of the product of step 1 (6.0 g) and TEA (5.1 ml) in CH$_2$Cl$_2$ (0.1 L). Stir at rt for 16 h, then add silica gel (approx 50 gm) and concentrate in vacuo. Purify the residue by flash chromatography on silica using EtOAc/hexane (1:4) to give a colorless solid (7.81 g, 92%) which can be crystallized from EtOAc/hexane (1:4).

Step 3:

Add titanium tetraisoproxide (7.5 ml) to a stirring solution of TiCl$_4$ (75 ml of 1N TiCl$_4$ in CH$_2$Cl$_2$) in CH$_2$Cl$_2$ (200 ml) at 0° C. After 15 min., add the product of step 2 (34.1 g), and 5 min. later add the imine from Method A, step 1 (66 g). Cool the reaction to −40° C., wait 20 min. and add diisopropyl ethylamine (35 ml). After 15 h at −40° C., cool the reaction to −70° C. and add isopropyl alcohol (250 ml). Gradually warm to rt over 6 h, then add 0.1N HCl (500 ml) and partition the reaction mixture with Et$_2$O. Wash (H$_2$O) and dry (MgSO$_4$) the organic layer, concentrate, and purify the residue by crystallization from CH$_3$OH to give a colorless solid (30.9 g, 46%).

Step 4:

Heat a solution of the product of step 3 (10 g) in toluene (0.5 l) to 90° C. and add N,O-bis(trimethylsilyl)acetamide (BSA) (7.4 ml). After 1 h, cool the reaction to 45° C. and add tetrabutylammonium fluoride (TBAF) (0.47 g). Periodically over the next 18 hr add additional BSA (a total of 3 molar equivalents) and continue stirring at 45° C. After a total time of 24 h, dilute the reaction with CH$_3$OH (150 ml) and stir at rt for 1 h. Concentrate the mixture in vacuo and purify by flash chromatography on silica using hexane/EtOAc (10:1) to elute the trans isomer. Continue to elute with hexane/EtOAc 5:1 to give the cis isomer.

Step 5: Separately treat solutions of the trans and cis isomers from step 4 in CH$_3$CN with aqueous HF according to the procedure of Method A, step 3, to give the trans and cis azetidinones 1 and 1 a, respectively.

1a: CIMS 394 (M+H) 100%; Elemental analysis calculated for C$_{23}$H$_{20}$NO$_2$SF: C 70.21, H 5.13, N 3.56, S 8.15; found C 70.33, H 5.43, N 3.71, S 8.20. 1H NMR CDCl$_3$: 2.78 (m, 4H), 4.52 (d, J=5 Hz, 1H), 5.23 (d, J=5 Hz, 1H), 6.82–7.3 (13H).

Using the procedure described in Example 1, method B, steps 3 and 4, use 4-methoxybenzylidene anisidine to prepare the following compounds:

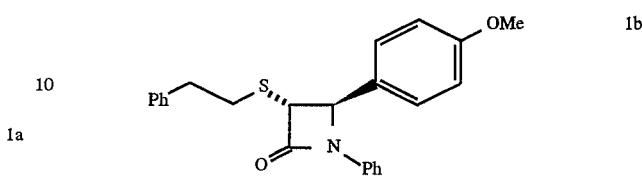

1b: Elemental analysis calculated for C$_{24}$H$_{23}$NO$_2$S: C 74.01, H 5.95, N 3.6, S 8.22; found C 74.19, H 6.0, N 3.73, S 8.03; [θ]232 nM=+3.4×10$^4$, [θ]248 nM=−3.07×10$^4$; 1H NMR CDCl$_3$: 2.95 (m, 4H), 3.82 (s, 3H), 3.95 (d, J=2.2 Hz, 1H), 4.72 (d, J=2.2 Hz, 1H), 6.9–7.3 (14H); SIMS 390 (M+H), 252 (100%).

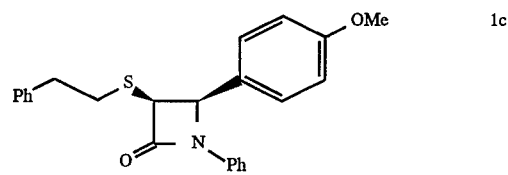

1c: 1H NMR CDCl$_3$: 2.78 (m, 4H), 3.8 (s, 3H), 4.53 (d, J=5.5 Hz, 1H), 5.27 (d, J=5.5 Hz, 1H), 6.9–7.3 (14H).

EXAMPLE 2

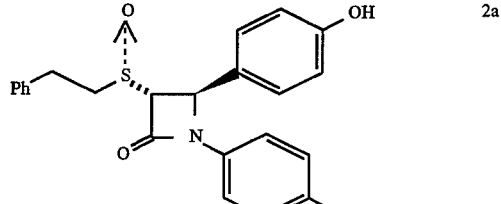

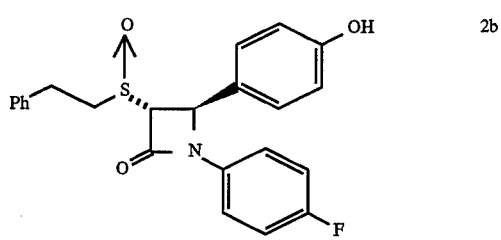

Heat a solution of compound 1 from Example 1 (2.3 g) and (1s)-(+)-(10-camphorsulfonyl)oxaziridine (1.48 g) in tetrahydrofuran (THF) (40 ml) to reflux. After 14 h, concentrate the reaction mixture and purify the residue by flash chromatography on silica using CH$_2$Cl$_2$/isopropyl alcohol (100:1) to elute first diastereomer 2a (0.6 g, 25%): Elemental analysis calculated for C$_{23}$H$_{20}$NO$_3$SF: C 67.47, H 4.92, N 3.42; found C 67.12, H 5.02, N 3.43; [θ]219 nM=−5.49×10$^4$, [θ]254 nM=+5.2×10$^4$; [θ]$_D^{25}$=+214.4° (1.25 mg/ml Ch$_3$OH); 1H NMR CDCl$_3$: 3.15 (m, 3H), 3.92 (m, 2H), 5.25 (d, J=2.5 Hz, 1H), 6.0 (bs, 1H), 6.8–6.9 (4H), 7.15–7.35 (8H); CIMS 410 (M+H). Next, elute diastereomer 2b, then crystallize diastereomer 2b from isopropyl alcohol (IPA) to give a colorless solid (1.48 g, 62%). Elemental analysis calculated for C$_{23}$H$_{20}$NO$_3$SF: C 67.47, H 4.92, N 3.42; found C 67.28, H 4.89, N 3.45; [θ]233 nM=+5.56×10$^4$,

[θ]251 nM=−2.79×10⁴; [α]_D^{25}=−16° (1.25 mg/ml CH₃OH); 1H NMR CDCl₃: 3.1–3.4 (m, 4H), 4.2 (d, J=2 Hz, 1H), 5.39 (d, J=2. Hz, 1H), 6.7 (d, 2H), 6.95 (m, 2H), 7.15–7.35 (8H); CIMS 410 (M+H).

Use the procedure from Example 2 with compound 1a from Example 1 to obtain the following compounds:

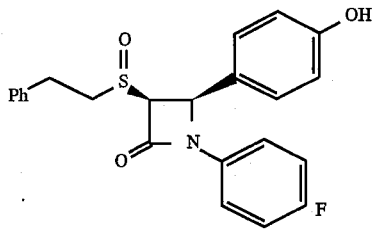

2c: Elemental analysis calculated for $C_{23}H_{20}NO_3SF$: C 67.47, H 4.92, N 3.42, S 7.83.; found C 67.21, H 5.0, N 3.5, S 7.48.

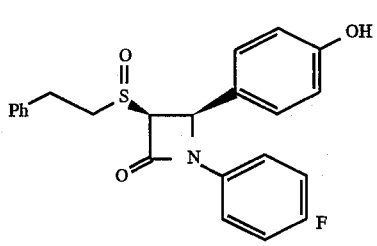

2d: Elemental analysis calculated for $C_{23}H_{20}NO_3SF$: C 67.47, H 4.92, N 3.42, S 7.83; found C 67.5, H 5.11, N 3.6, S 7.71.

EXAMPLE 3

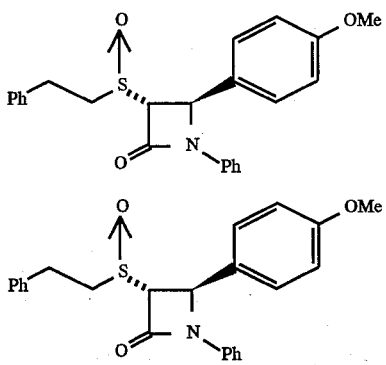

Treat compound 1b from Example 1 (0.36 g) in CH₂Cl₂ (15 ml) at 0° C. with m-chloroperbenzoic acid (mCPBA) (0.16 g) at −78° C. After 2 h, add dilute NaHSO₃ and warm the mixture to rt. Partition with EtOAc and sequentially wash the organic layer with 10% NaHCO₃ and brine, then dry (MgSO₄) and concentrate in vacuo. Purify the residue by HPLC on silica using EtOAc/hexane (1:2) to elute compounds 3a (0.185 g) and 3b (0.10 g).

3a: Elemental analysis calculated for $C_{24}H_{23}NO_3S$: C 71.09, H 5.72, N 3.45: found C 70.87, H 5.55, N 3.52; [θ]220 nM=−5.36×10⁴, [θ]257 nM=+5.46×10⁴; 1H NMR CDCl₃: 3.15 (m, 3H), 3.8 (s, 3H) 3.9 (m, 1H), 3.94 (d, J=2.5 Hz, 1H), 5.33 (d, J=2.5 Hz, 1H), 6.9–7.35 (14H).

3b: Elemental analysis calculated for $C_{24}H_{23}NO_3S$: C 71.09, H 5.72, N 3.45, S 7.83; found C 70.90, H 5.72, N 3.55; [θ]220 nM=−4.8×10³, [θ]233 nM=+7.4×10⁴, [θ]250 nM=−4.0×10⁴; 1H NMR CDCl₃: 3.18 (m, 4H), 3.8 (s, 3H), 4.12 (d, J=2 Hz, 1H), 5.5 (d, J=2 Hz, 1H), 6.9–7.35 (14H)

Use the procedure of example 3 with compound 1c obtain the following products:

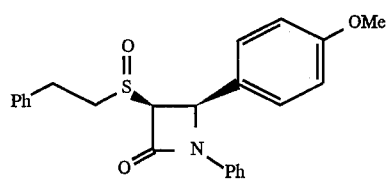

3c: Elemental analysis calculated for $C_{24}H_{23}NO_3S \cdot 0.2\ H_2O$: C 70.46, H 5.77, N 3.42; found C 70.49, H 5.78, N 3.52; 1H NMR CDCl₃: 2.85 (m, 1H), 2.95 (m, 1H), 3.12 (m, 1H), 3.62 (m, 1H), 3.8 (s, 3H), 4.4 (d, J=5.6 Hz, 1H), 5.35 (d, J=5.6 Hz, 1H), 6.9–7.35 (14H).

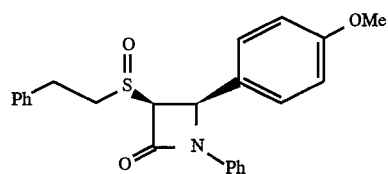

3d: Elemental analysis calculated for $C_{24}H_{23}NO_3S \cdot 0.2\ H_2O$: C 70.46, H 5.77, N 3.42; found C 70.32, H 5.78, N 3.46; 1H NMR CDCl₃: 3.17 (m, 3H), 3.4 (m, 1H), 3.88 (s, 3H), 4.69 (d, J=5.2 Hz, 1H), 5.55 (d, J=5.2 Hz, 1H), 6.95–7.4 (14H); $[α]_D^{25}=−136°$ (CH₃OH).

EXAMPLE 4

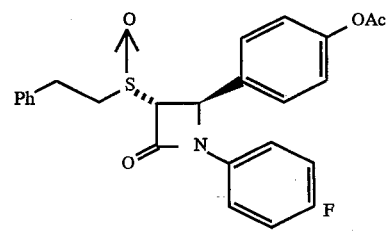

Treat compound 2b (60 mg) in CH₂Cl₂ (5 ml) with TEA (0.025 ml) and acetic anhydride (0.017 ml). After 2 h, concentrate the reaction mixture and purify the residue by flash chromatography on silica using EtOAc/hexane (1:1). to give a white solid. Elemental analysis calculated for $C_{25}H_{22}NO_4SF$: C 66.5, H 4.91, N 3.1, S 7.1; found C 66.28, H 5.10, N 3.29, S 6.99.

Use the above procedure for preparing compound 4 with compounds 2c and 2d to obtain the following products 4a and 4b, respectively:

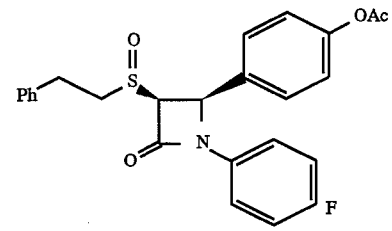

4a: Elemental analysis calculated for $C_{25}H_{22}NO_4SF$: C 66.5, H 4.91, N 3.1, S 7.1; found C 66.36, H 5.13, N 3.23, S 7.02; 1H NMR CDCl₃: 2.32 (s, 3H), 2.92 (m, 2H), 3.14 (m, 1H), 3.7 (m, 1H), 4.42 (d, J=5.7 Hz, 1H), 5.38 (d, J=5.8 Hz, 1H), 7.0 (m, 2H), 7.12–7.35 (9H), 7.44 (d, 2H).

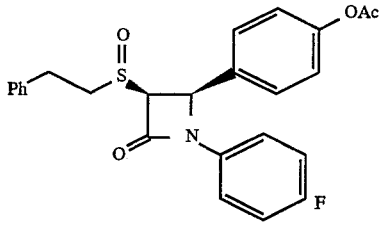

4b: 1H NMR CDCl₃: 2.32 (s, 3H), 3.15 (m, 3H), 3.38 (m, 1H), 4.72 (d, J=5.3 Hz, 1H), 5.58 (d, J=5.2 Hz, 1H), 7.0 (m, 2H), 7.15–7.35 (9H), 7.40 (d, 2H).

EXAMPLE 5

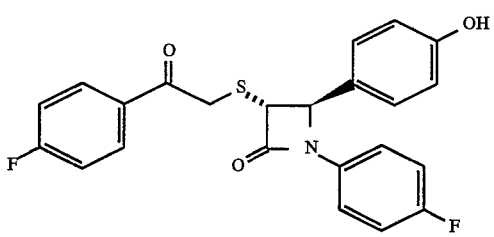

Step 1:
Add TEA (14 ml) to a mixture of 4-methoxybenzylchloride (13 ml) and ethyl-2-mercaptoacetate (10 ml) in CH₂Cl₂ (0.2 L) under N₂. After 48 h, dilute the reaction with Et₂O(0.5 L) and sequentially wash the organic phase with 0.3N HCl (3x) and 10% NaHCO₃. Dry and concentrate the organic layer to give an oil (22 g). Dissolve a portion of the oil (5 g) in THF (75 ml) and water (75 ml) and add LiOH (1 g). After stirring for 72 h, dilute the reaction with water (0.15 L) and extract with hexane (0.2 L). Acidify the aqueous phase with 1N HCl and extract with EtOAc. Wash (H₂O), and dry (MgSO₄) the organic layer and concentrate to give a yellow solid (4.25 g, 96%).

Step 2:
Treat a mixture of the product of step 1 (1 g) and the imine from Example 1, Method A, step 1 (1.55 g) in CH₂Cl₂ (40 ml) with dimethylamino phosphoryldichloride (0.56 ml) at 0° C. Warm to rt and stir for 16 h. Dilute the reaction with Et₂O (100 ml) and wash sequentially with 1N HCl, 10% NaHCO and brine. Dry (MgSO₄) and concentrate the organic phase and purify the resultant residue by flash chromatography on silica using hexane:EtOAc (20:1) to yield an oil (0.75 g, 30%).

Step 3:
Add mercuric acetate (121 mg) to a solution of the product of step 2 (0.2 g) in trifluoroacetic acid (5 ml) at 0° C. After 15 min., partition the reaction mixture between H₂O and Et₂O. Wash, dry and concentrate the organic layer and purify the residue by flash chromatography on silica using hexane:EtOAc (10:1) to give an oil (0.15 g).

Step 4:
Add 2-bromo-4'-fluoroacetophenone (86 mg) to a mixture of the product of step 3 (0.15 g) and TEA (0.06 ml) in CH₂Cl₂ (5 ml) at rt under N₂. After 5 h, dilute the reaction with Et₂O and wash sequentially with 1N HCl, 10% NaHCO₃ and brine. Dry and concentrate the organic layer and purify the residue by flash chromatography on silica using hexane:EtOAc (9:1) to give an oil. Resolve this by HPLC using a Chiralcel AS column with hexane:IPA (85:15) to elute enantiomer 5(1) ([θ]228 nM=−3.77×10³, [θ]244 nM=+3.34×10³) and then enantiomer 5(2) ([θ]228 nM=+3.65×10³, [θ]244 nM=−3.24×10³).

Step 5:
Treat enantiomer 5(2) with HF according to the procedure of Example 1, Method A, step 3, to obtain compound 5. Elemental analysis calculated for C₂₃H₁₇NO₃SF₂: C 64.93, H 4.03, N 3.29, S 7.52; found C 64.87, H 4.39, N 3.31, S 7.25.

EXAMPLE 6

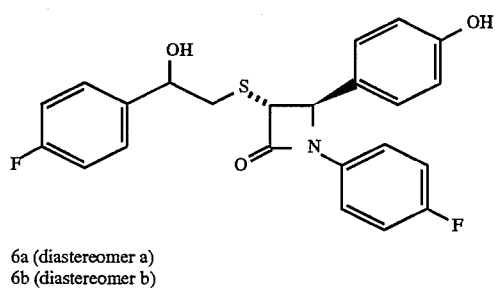

6a (diastereomer a)
6b (diastereomer b)

Step 1:
Add NaBH₄ (28 mg) to a solution of enantiomer 5 (2) from step 4 of Example 5 (0.4 g) in CH₃OH (20 ml). After 2 h, partition the reaction mixture between Et₂O and H₂O. Dry and concentrate the organic layers and purify the residue by flash chromatography using EtOAc:hexane (1:6) to give diastereomers 6(1) and 6(2).

Step 2:
Individually treat diastereomers 6(1) and 6(2) from step 1 with HF according to the procedure of Example 1, Method A, step 3, to obtain 6a and 6b.

6a: 1H NMR in CDCl₃: 2.85 (dd, J=6, 12 Hz, 1H), 3.04 (dd, J=3, 12 Hz, 1H), 4.06 (d, J=2.4 Hz, 1H), 4.7 (d, J=2.4 Hz, 1H), 4.9 (d, J=3, 9 Hz, 1H), 6.85–7.35 (12H).

6b: 1H NMR in CDCl₃ : 3.01 (m, 2H), 3.97 (d, J=2.2 Hz, 1H), 4.7 (d, J=2.2 Hz, 1H), 4.92 (d, J=4, 8 Hz, 1H), 6.85–7.36 (12H).

EXAMPLE 7

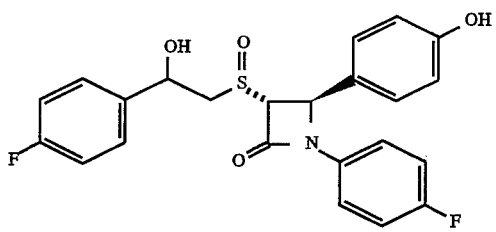

7a: diastereomer a
7b: diastereomer b
7c: diastereomer c
7d: diastereomer d

Step 1:
Treat diastereomer 6(1) from Example 6, step 1, with mCPBA as described in Example 3. Purify the products by HPLC on silica gel, eluting with EtOAc:hexane (1:2) to obtain diastereomers 7(1) and 7(2).

Step 2:
Individually treat diastereomers 7(1) and 7(2) from step 1 with HF as described in Example 1, Method A, step 3, to obtain 7a and 7b.

1H NMR CDCl₃ with 10% CD₃OD:

7a: 3.35 (d, 1H), 3.75 (dd, 1H), 4.22 (s, 1H), 5.20 (m, 2H), 6.80 (d, 2H), 6.9 (m, 2H), 7.04 (m, 2H), 7.24 (m, 4H), 7.38 (m, 2H).

7b: 3.02 (dd, 1H), 3.26 (m, 1H), 4.21 (d, J=2.1 Hz, 1H) 5.14 (dd, 1H), 5.41 (d, J=2.1 Hz, 1H), 6.78 (d, 2H), 6.9 (m, 2H), 6.98 (m, 2H), 7.18 (m, 4H), 7.28 (m, 2H).

Using the procedures of steps 1 and 2, treat diastereomer 6(2) from Example 6, step 1, to obtain 7c and 7d.
1H NMR CDCl$_3$ with 10% CD$_3$OD:
7c: 3.12 (dd, 1H), 3.30 (m, 1H), 4.45 (d, J=2.2 Hz, 1H) 5.04 (dd, 1H), 5.39 (d, J=2.2 Hz, 1H), 6.78 (d, 2H), 6.88 (m, 2H), 6.94 (m, 2H), 7.20 (m, 6H).
7d: 3.10 (dd, 1H), 3.72 (m, 1H), 4.07 (d, J=2.5 Hz, 1H), 5.09 (dd, J=2.3, 11.0 Hz, 1H), 5.17 (d, J=2.5 Hz, 1H), 6.78 (d, 2H), 6.85 (m, 2H), 6.98 (m, 2H), 7.18 (m, 4H), 7.30 (m, 2H).

EXAMPLE 8

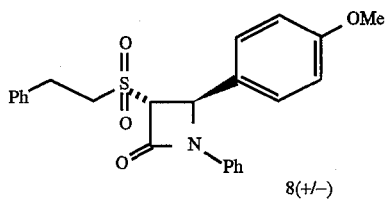

8(+/−)

Treat a solution of the racemic product from Example 1, Method A, step 2 (0.185 g) in CH$_2$Cl$_2$ (20 ml) with mCPBA. After 3 h, add NaHSO$_3$ and NaHCO$_3$ and stir for 10 minutes, then extract with EtOAc. Purify the organic fraction by flash chromatography on silica using hexane:EtOAc (4:1) to give compound 8 as a white solid (0.15 g, 76%). Elemental analysis calculated for C$_{24}$H$_{23}$NO$_4$S: C 68.39, H 5.5, N 3.32; found C 68.12, H 5.49, N 3.37. EIMS 421 (M+). 1H NMR: 3.2 (m, 2H), 3.55 (m, 2H), 3.80 (s, 3H), 4.23 (d, J=2.4 Hz, 1H), 5.53 (d, J=2.4 Hz, 1H) (d, 2H), 7.1 (m, 1H), 7.28 (11H).

EXAMPLE 9

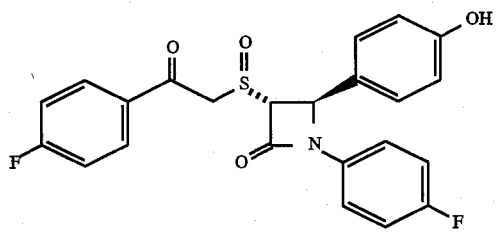

9a: diastereomer a
9b: diastereomer b

Step 1:
Treat the product from Example 5, step 4, enantiomer 5(2) according to the procedure of Example 3. Purify the product by flash chromatography using EtOAc:hexane (1:3) to yield diastereomer 9(1) and diastereomer 9(2).

Step 2:
Individually treat diastereomers 9(1) and 9(2) from step 1 with HF according to the procedure of Example 1, Method A, step 3, to obtain 9a and 9b.

9a: 1H NMR in CDCl$_3$: 4.39 (d, J=2.4 Hz, 1H), 4.93 (d, J=16 Hz, 1H), 5.25 (d, J=16 Hz, 1H), 5.32 (d, J=2.4 Hz, 1H), 5.55 (bs, 1H), 6.85–6.95 (m, 4H) 7.18–7.30 (m, 6H), 8.05–8.09 (m, 2H).

9b: 1H NMR in CDCl$_3$ with 5% CD$_3$OD: 4.39 (d, J=2.1 Hz, 1H), 4.46 (d, J=15 Hz, 1H), 4.62, (d, J=15 Hz, 1H), 5.42 (d, J=2.1 Hz, 1H), 6.75 (d, 2H), 6.9 (dd, 2H), 7.08–7.20 (m, 6H), 7.90 (m, 2H).

The following formulations exemplify some of the dosage forms of this invention. In each the term "active compound" designates a compound of formula I.

EXAMPLE A

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Methods of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Representative formulations comprising a cholesterol biosynthesis inhibitor are well known in the art. It is contemplated that where the two active ingredients are administered as a single composition, the dosage forms disclosed above for substituted azetidinone compounds may readily be modified using the knowledge of one skilled in the art.

Using the test procedures described above, the following in vivo data were obtained for the exemplified compounds. Data is reported as percent change (i.e., percent reduction in cholesterol esters) versus control, therefore, negative numbers indicate a positive lipid-lowering effect.

| | % Reduction | | | | % Reduction | | |
|---|---|---|---|---|---|---|---|
| Ex. # | Serum Cholest. | Cholest. Esters | Dose mg/kg | Ex. # | Serum Cholest. | Cholest. Esters | Dose mg/kg |
| 1 | −27 | −83 | 1 | 3c | −35 | −93 | 3 |
| 1a | 0 | 0 | 1 | 3d | −18 | −78 | 3 |
| 1b | −56 | −97 | 3 | 4 | −28 | −83 | 1 |
| 1c | 0 | −31 | 10 | 4a | −22 | −55 | 1 |
| 2a | −9 | −56 | 1 | 4b | −14 | −24 | 1 |
| 2b | −28 | −82 | 1 | 5 | −42 | −97 | 1 |
| 2c | −7 | −40 | 1 | 6a | −42 | −95 | 1 |
| 2d | −11 | −42 | 1 | 6b | −38 | −95 | 1 |
| 3a | −12 | −58 | 1 | 8 | 0 | −54 | 25 |
| 3b | −20 | −82 | 1 | | | | |

We claim:

1. A compound represented by the formula

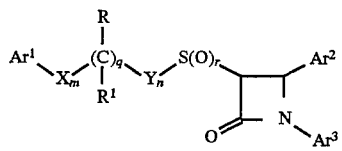

or a pharmaceutically acceptable salt thereof, wherein:

$Ar^1$ is aryl or $R^{10}$-substituted aryl;

$Ar^2$ is aryl or $R^4$-substituted aryl;

$Ar^3$ is aryl or $R^5$-substituted aryl;

X and Y are independently selected from the group consisting of —$CH_2$—, —CH(lower alkyl)— and —C(dilower alkyl)—;

R is —$OR^6$, —$O(CO)R^6$, —$O(CO)OR^9$ or —$O(CO)NR^6R^7$; $R^1$ is hydrogen, lower alkyl or aryl; or R and $R^1$ together are =O;

q is 0 or 1;

r is 0, 1 or 2;

m and n are independently 0, 1, 2, 3 or 4; provided that the sum of m, n and q is 2, 3 or 4;

$R^4$ is 1–5 substituents independently selected from the group consisting of lower alkyl, —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}CONR^6R^7$, —(lower alkylene)$COOR^6$ and —CH=CH—$COOR^6$;

$R^5$ is 1–5 substituents independently selected from the group consisting of —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}CONR^6R^7$, —$CF_3$, —CN, —$NO_2$, halogen, —(lower alkylene)$COOR^6$ and —CH=CH—$COOR^6$;

$R^6$, $R^7$ and $R^8$ are independently selected from the group consisting of hydrogen, lower alkyl, aryl and aryl-substituted lower alkyl;

$R^9$ is lower alkyl, aryl or aryl-substituted lower alkyl; and $R^{10}$ is 1–5 substituents independently selected from the group consisting of lower alkyl, —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}CONR^6R^7$, —$CF_3$, —CN, —$NO_2$ and halogen.

2. A compound of claim 1 wherein q is zero.

3. A compound of claim 1 wherein q is 1.

4. A compound of claim 2 wherein $Ar^1$ is phenyl or $R^{10}$-substituted phenyl, $Ar^2$ is $R^4$-substituted phenyl and $Ar^3$ is phenyl or $R^5$-substituted phenyl.

5. A compound of claim 2 wherein X and Y are each —$CH_2$— and the sum of m and n is 2, 3 or 4.

6. A compound of claim 4 wherein X and Y are each —$CH_2$—, and the sum of m and n is 2, 3 or 4.

7. A compound of claim 3 wherein $Ar^1$ is phenyl or $R^{10}$-substituted phenyl, $Ar^2$ is $R^4$-substituted phenyl and $Ar^3$ is phenyl or $R^5$-substituted phenyl.

8. A compound of claim 3 wherein X and Y are each —$CH_2$— and the sum of m and n is 1, 2 or 3.

9. A method of lowering serum cholesterol levels in a mammal in need of such treatment comprising administering an effective amount of a compound of claim 1.

10. A compound of claim 7 wherein X and Y are each —$CH_2$—; the sum of m and n is 1, 2 or 3; and $R^1$ is hydrogen and R is —$OR^6$, wherein $R^6$ is hydrogen, or wherein R and $R^1$ together form a =O group.

11. A compound of claim 10 wherein m is zero and n is 1.

12. A compound of claim 2 selected from the group consisting of trans-1-(4-fluorophenyl)-4-(4-hydroxyphenyl)-3-[(2-phenylethyl)-thio]-2-azetidinone;

trans-4-(4-methoxyphenyl)-1-phenyl-3-[(2-phenylethyl)thio]-2-azetidinone;

cis-4-(4-methoxyphenyl)-1-phenyl-3-[(2-phenylethyl)thio]-2-azetidinone;

trans-1-(4-fluorophenyl)-4-(4-hydroxyphenyl)-3-[(2-phenylethyl)sulfinyl]-2-azetidinone;

cis-1-(4-fluorophenyl)-4-(4-hydroxyphenyl)-3-[(2-phenylethyl)sulfinyl]-2-azetidinone;

trans-4-(4-methoxyphenyl)-1-phenyl-3-[(2-phenylethyl)sulfinyl]-2-azetidinone;

cis-4-(4-methoxyphenyl)-1-phenyl-3-[(2-phenylethyl)sulfinyl]-2-azetidinone;

trans-4-[1-(4-fluorophenyl)-4-oxo-3-[(2-phenylethyl)sulfinyl]-2-azetidinyl]-phenyl acetate;

cis-4-[1-(4-fluorophenyl)-4-oxo-3-[(2-phenylethyl)sulfinyl]-2-azetidinyl]-phenyl acetate; and (+/−)-trans-4-(4-methoxyphenyl)-1-phenyl-3-[(2-phenylethyl)sulfonyl]-2-azetidinone.

13. A compound of claim 3 selected from the group consisting of
- trans-1-(4-fluorophenyl)-3-[[2-(4-fluorophenyl)-2-oxoethyl]thio]-4-(4-hydroxyphenyl)-2-azetidinone; and
- trans-1-(4-fluorophenyl)-3-[[2-(4-fluorophenyl)-2-hydroxyethyl]thio]-4-(4-hydroxyphenyl)-2-azetidinone.

14. A method of lowering cholesterol levels in a mammal in need of such treatment comprising administering an effective amount of a compound of claim 1.

15. A pharmaceutical composition comprising a cholesterol-lowering effective amount of a compound of claim 1 in a pharmaceutically acceptable carrier.

* * * * *